United States Patent
Rehe et al.

(10) Patent No.: US 11,209,640 B2
(45) Date of Patent: Dec. 28, 2021

(54) LENS FOR A DISTAL END OF AN OPTICAL CHANNEL OF AN ENDOSCOPE SHAFT

(71) Applicant: Henke-Sass, Wolf GmbH, Tuttlingen (DE)

(72) Inventors: Oliver Rehe, Wurmlingen (DE); Andreas Mattes, Duerbheim (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 506 days.

(21) Appl. No.: 15/974,676

(22) Filed: May 8, 2018

(65) Prior Publication Data
US 2018/0329197 A1 Nov. 15, 2018

(30) Foreign Application Priority Data

May 9, 2017 (DE) .......................... 102017109913.1

(51) Int. Cl.
G02B 23/24 (2006.01)
A61B 1/00 (2006.01)
A61B 1/07 (2006.01)
G02B 7/02 (2021.01)

(52) U.S. Cl.
CPC ........ G02B 23/243 (2013.01); A61B 1/00096 (2013.01); A61B 1/00179 (2013.01); G02B 7/021 (2013.01); G02B 23/2476 (2013.01); A61B 1/07 (2013.01)

(58) Field of Classification Search
CPC ............ G02B 23/2476; G02B 23/2484; G02B 23/243; A61B 1/0009; A61B 1/00163
See application file for complete search history.

(56) References Cited

U.S. PATENT DOCUMENTS

| 5,377,669 | A | 1/1995 | Schulz |
| 6,503,196 | B1 | 1/2003 | Kehr et al. |
| 6,547,721 | B1 * | 4/2003 | Higuma ................. A61L 2/07 600/133 |
| 6,767,322 | B1 * | 7/2004 | Futatsugi ........... A61B 1/00096 600/129 |
| 2002/0128535 | A1 * | 9/2002 | Kikuchi ............... A61B 1/0011 600/101 |
| 2002/0128539 | A1 | 9/2002 | Higuma et al. |
| 2002/0186478 | A1 | 12/2002 | Watanabe et al. |
| 2006/0268400 | A1 | 11/2006 | Weyh et al. |
| 2014/0275786 | A1 | 9/2014 | Goto et al. |
| 2016/0062127 | A1 | 3/2016 | Gittler et al. |

FOREIGN PATENT DOCUMENTS

DE 19502006 A1 8/1996
JP 2003230534 A 8/2003

* cited by examiner

*Primary Examiner* — Matthew J Kasztejna
(74) *Attorney, Agent, or Firm* — Skaar Ulbrich Macari, P.A.

(57) ABSTRACT

A lens for a distal end of an optical channel of an endoscope shaft is provided, wherein the lens defines an outer side and an inner side as well as a circumferential surface connecting the two sides, wherein a light-absorbing coating is applied to the circumferential surface and an area of the inner side connected thereto, and wherein a solderable layer is applied to the light-absorbing coating in the area of the circumferential surface with the result that the lens can be soldered in the distal end such that the distal end is sealed.

9 Claims, 2 Drawing Sheets

LENS FOR A DISTAL END OF AN OPTICAL CHANNEL OF AN ENDOSCOPE SHAFT

PRIORITY

This application claims the benefit of German Patent Application No. 102017109913.1, filed on May 9, 2017, which is hereby incorporated herein by reference in its entirety.

FIELD

The present invention relates to a lens for a distal end of an optical channel of an endoscope shaft, wherein the lens comprises an outer side and an inner side as well as a circumferential surface connecting the two sides.

BACKGROUND

Lenses for the distal end of the optical channel of endoscope shafts can be soldered in the distal end of an endoscope in order to seal the distal end. An otherwise customary additional optical flat, which would otherwise implement the distal sealing, can thereby be dispensed with.

It has been shown, however, that in the case of the variant of sealing the distal end with a lens, the quality of the imaging of the whole endoscope lens system no longer completely satisfies the ever-increasing demands.

SUMMARY

An object of certain embodiments of the invention is to provide an improved lens for sealing a distal end of an optical channel of an endoscope shaft.

The lens according an example embodiment for a distal end of an optical channel of an endoscope shaft comprises an outer side, an inner side as well as a circumferential surface connecting the two sides, wherein a light-absorbing coating is applied to the circumferential surface and an area of the inner side connected thereto (or directly joining it). In addition, a solderable layer is applied to the light-absorbing coating in the area of the circumferential surface. It is thus possible to solder the lens in the distal end such that the distal end is sealed. Since the light-absorbing coating is formed on the circumferential surface and the area of the inner side connected thereto, veiling glare and scattered light are suppressed excellently with the result that the contrast of the imaging of the whole endoscope lens system can be improved and undesired double and ghost images can be suppressed.

The lens is preferably a lens with negative refractive power. The inner side of the lens can comprise a curved portion (e.g. concavely curved). The curved portion, which is required for the imaging, is not provided with the light-absorbing coating, of course. The light-absorbing coating is preferably applied in an area of the inner side which borders on the curved portion and preferably surrounds it.

The light-absorbing coating can be a metallic coating. In particular, it can contain chromium.

The circumferential surface and the area of the inner side connected thereto, to which the light-absorbing coating is applied, can be roughened or have a matte structure (e.g. a frosted glass effect). This can be achieved, e.g., in that they have been ground but not polished. Together with the light-absorbing coating, a matte-absorbing coating can thus be provided. The light-absorbing coating is preferably black. A matte black layer or matte black surface for light absorption can thus be provided.

The portion of the light-absorbing coating formed on the circumferential surface can form (e.g. in a sectional view) an angle which lies in the range of from 80° to 100° and preferably in the range of from 85 to 95° and particularly preferably in the range of from 88 to 92° with the portion of the light-absorbing coating formed on the area of the inner side connected to (or following) the circumferential surface. In particular, the angle can be 90°, 91° or 89°.

The portion of the light-absorbing coating formed on the area of the inner side connected to the circumferential surface can be annular seen in a top view onto the inner side.

The shape of the light-absorbing coating can be described as a hollow cylinder with a base comprising an opening. The portion of the light-absorbing coating which is formed on the circumferential surface forms the wall of the hollow cylinder and the portion of the light-absorbing coating which is formed on the area of the inner side connected to the circumferential surface forms the base with the opening. Of course, the opening in the base is situated such that the lens can achieve its intended imaging property. In particular, the inner side comprises a concavely curved portion which is not covered with the light-absorbing coating.

The light-absorbing coating can be formed as a single layer or as a multi-ply layer. In the same way, the solderable layer can be formed as an individual layer or as a multi-ply layer system. The outermost layer of the solderable layer preferably comprises gold.

The lens (and a lens system) can be designed in particular for the visible wavelength range (i.e. wavelengths from 400 to 700 nm) and optionally also for the near infra-red range (wavelengths from 710 to 3000 nm, 710 to 900 nm or 780 to 900 nm).

The lens can be formed as a plano-concave lens. The concave curvature is preferably a spherical curvature. However, it can also be an aspherical curvature. The concave curvature is preferably formed on the inner side of the lens. The planar side is preferably the outer side of the lens. However, the outer side of the lens can also be spherically or aspherically curved (e.g. concave or convex).

The lens is preferably formed in one piece. It can be formed from sapphire.

The lens can include an anti-reflection coating on its outer side and/or its inner side. The anti-reflection coating is preferably formed only in areas in which no light-absorbing coating is applied.

Furthermore, an endoscope with an endoscope shaft is provided herein. The endoscope or endoscope shaft can include an optical channel comprising a distal end, wherein a lens as described in this application is soldered in the distal end via the solderable layer such that the distal end is sealed. The lens can be part of an objective. Furthermore, yet further optical elements can be arranged in the optical channel, such as e.g. an inversion system, which can be formed e.g. as a rod lens system.

The inner side comprising the concave curvature preferably faces the further elements of the objective or of the optical channel. The planar outer side preferably faces an object to be imaged.

The endoscope shaft can be formed in particular as a rigid shaft.

By sealing the distal end is meant in particular that the distal end is liquid-tight and that it is autoclavable.

Furthermore, an endoscope lens system for an endoscope is provided. The endoscope lens system can include an optical channel (or optical tube) comprising a distal end and a lens as described herein and wherein the lens is soldered in the distal end via the solderable layer such that the distal end is sealed.

The endoscope is preferably a forward view endoscope or an endoscope with an oblique direction of view. Furthermore, the endoscope can be formed such that the angle of the direction of view is adjustable.

It is understood that the features named above and those yet to be explained below can be used not only in the stated combinations but also in other combinations or alone, without departing from the scope of the present invention.

Figure 1:
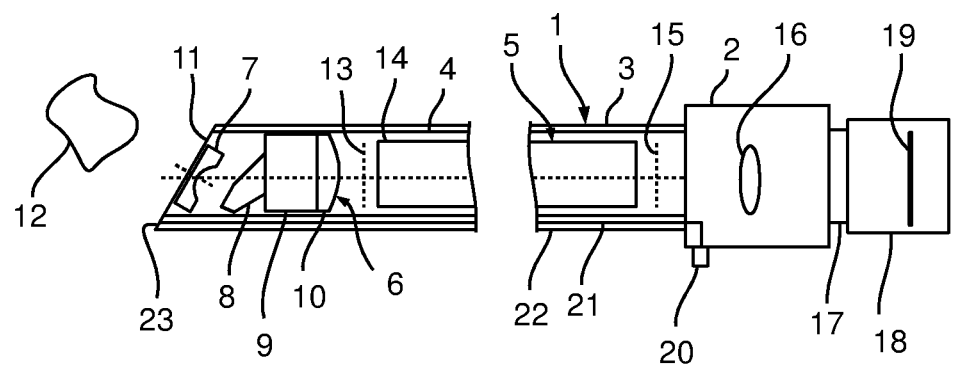
FIG. 1 is a schematic sectional view of a first embodiment example of the endoscope in accordance with certain example embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

The invention is explained in yet more detail below with the aid of embodiment examples with reference to the attached drawings, which also disclose features essential to the invention. These embodiment examples merely serve the purpose of illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components. Elements or components of different embodiment examples can be combined with each other, unless otherwise indicated. Modifications and alterations which are described for one of the embodiment examples can also be applicable to other embodiment examples. To avoid repetitions, the same or corresponding elements are given the same reference numbers in different figures and are not explained repeatedly.

In the embodiment example shown in FIG. 1, the endoscope 1 according to the invention, which can be formed e.g. as an arthroscope, comprises a main part 2 and a shaft 3 connected thereto.

An optical tube 4, in which an endoscope lens system 5 is arranged, extends in the shaft 3. The endoscope lens system 5 comprises an objective 6 with a first lens 7, a deflecting prism 8 as well as a second and third lens 9, 10, which images an object 12 located in front of a distal end 11 of the optical tube 4 as a distal intermediate image in a distal intermediate image plane 13. Furthermore, the endoscope lens system 5 comprises an inversion system 14, which images the distal intermediate image from the distal intermediate image plane 13 into a proximal intermediate image plane 15 as a proximal intermediate image. The inversion system can be formed e.g. as a rod lens system and carry out one or more intermediate imagings in order to generate the desired proximal intermediate image.

A further lens system 16 (e.g. eyepiece 16) can be arranged in the main part 2. A camera connection 17, to which a camera 18 is releasably secured, can be provided at the end of the main part 2 facing away from the shaft 3. The camera 18 can comprise a lens system (not shown) as well as a two-dimensional image sensor 19. The image sensor 19 can, for example, be a CCD sensor or a CMOS sensor. The camera does not have to be connected to the camera connection 17 directly, as is shown in FIG. 1. It is also possible for a coupler (not shown), which can itself contain a lens system, to be interposed between camera connection 17 and the camera 18.

On the main part 2, a lighting connection 20 is formed, which is connected to optical fibres 21 (of which only one is drawn in representatively in FIG. 1), which extend from the lighting connection 20 through an area between an outer tube 22 of the shaft 3 and the optical tube 4 to the distal end 23 of the shaft 3 and there emit the light for the illumination of the object 6.

Figure 2:
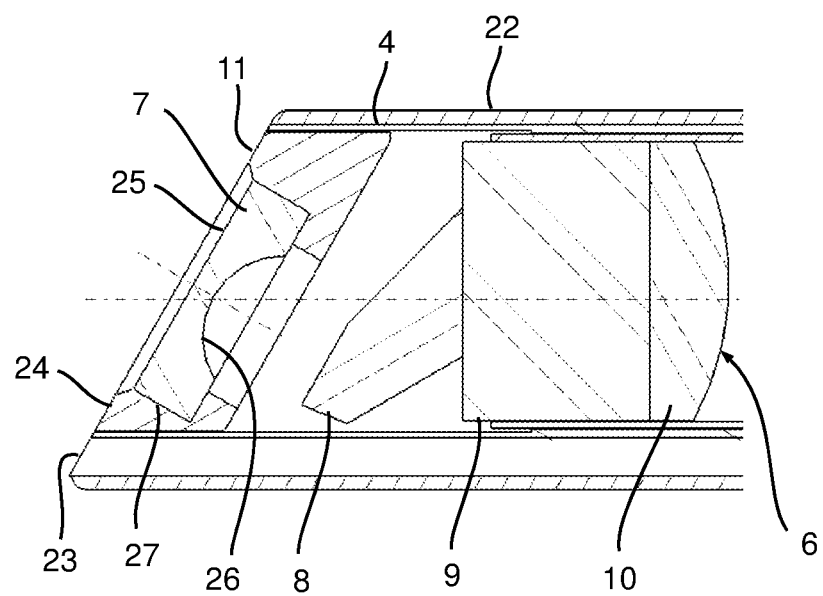
FIG. 2 is an enlarged sectional view of the distal end of the endoscope shaft of the endoscope from FIG. 1.

As is shown in FIG. 2 in the enlarged detail view of the objective 6 in the distal end area of the shaft 3, the distal end 11 of the optical tube 4 comprises a socket 24 (which is e.g. welded or soldered to the optical tube 4), into which the first lens 7 is soldered with the result that the first lens 7 seals the distal end 11 of the optical tube 4. No moisture, for example, can thereby enter the optical tube 4 (which can also be referred to as optical channel 4) via the distal end 11. In particular, autoclaving of the endoscope shaft 3 is thereby possible.

The first lens 7 comprises a planar or curved outer side 25, an inner side 26 with concave curvature as well as a circumferential surface 27 connecting the two sides. The planar outer side 25 or the curved outer side 25 as well as the concavely curved inner side 26 are formed such that the first lens 7 has a negative focal length.

Figure 3:
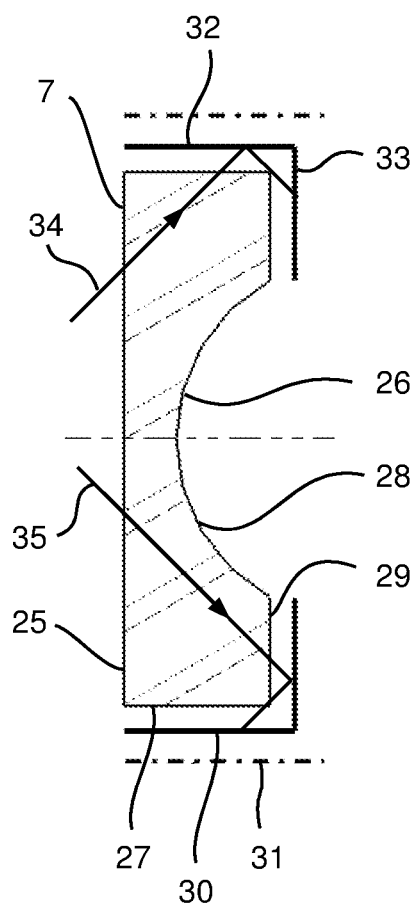
FIG. 3 is an enlarged sectional view of the lens of the objective according to FIGS. 1 and 2.

As is to be seen in particular in the enlarged detail view of the first lens 7 in FIG. 3, the first lens 7 is formed in one piece. It is preferably formed as a sapphire lens 7.

Through the first lens 7, large angles of view are possible and an otherwise customary optical flat for sealing the distal end 11 can be dispensed with, since this sealing is realized by the first lens 7 soldered into the socket 24 in the manner described. In addition, the first lens 7 is scratch-resistant since it is made from sapphire.

The inner side 26 comprises a concavely curved first area 28 located in the centre and a second area 29 surrounding this first area 28 in an annular manner. The first area 28 of the inner side 26 as well as the outer side 25 are polished since they are used for the optical imaging. In contrast, the second area 29 is not polished but is only ground and thus comprises a matte or a rough-matte surface structure. It can also be said that the second area 29 has a frosted glass effect or milk glass effect.

For the suppression of scattered light, a light-absorbing coating 30 is applied to the circumferential surface 27 and to the second area 29 of the inner side 26 directly bordering thereon. The light-absorbing coating 30 can, in particular, be a metallic coating. The light-absorbing coating 30 can be a single layer or a layer structure made up of several individual layers. The light-absorbing coating 30 can also be referred to as blackening. For example, the light-absorbing coating 30 can be formed as a black chromium coating.

Since the light-absorbing coating 30 is applied to the circumferential surface 27 with the rough-matte surface structure and to the second area 29 with the rough-matte surface structure, a matte black layer or matte black surface is present which excellently absorbs undesired light.

In the area of the circumferential surface 27, a solderable layer 31 is applied to the light-absorbing coating 30, wherein the light-absorbing coating 30 (and in particular the matte-black character thereof) is preserved underneath. The solderable layer 31 can be a single layer or can comprise several partial layers. When it is a single layer, the solderable layer is preferably formed as a gold layer. When the solderable layer 31 comprises several partial layers, the outermost partial layer is preferably a gold layer. The provision of the gold layer is advantageous for the soldering since it does not oxidize during the soldering.

The light-absorbing coating 30 and the solderable layer 31 are shown in FIG. 3 in the manner of an exploded representation. Of course, the light-absorbing coating 30 is applied to the circumferential surface 27 and to the second area 29 without the spacing shown and the solderable layer 31 is applied to the light-absorbing coating 30 without the spacing shown.

Through the described structure of the first lens 7, the first lens 7 can be soldered into the socket 24 with the result that the distal end 11 of the optical tube 4 can be formed hermetically sealed.

Figure 4:
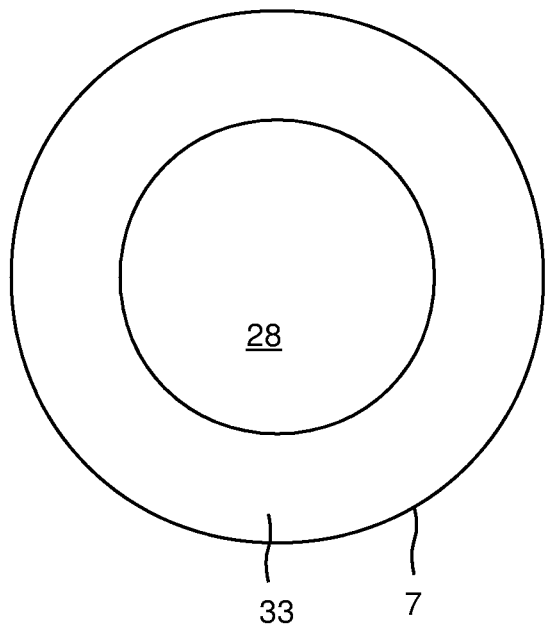
FIG. 4 is a top view onto the inner side of the lens.

As is readily recognizable in the sectional representation according to FIG. 3 as well as in the top view onto the inner side 26 in FIG. 4, the light-absorbing coating 30 comprises a first portion 32 (which extends linearly in the direction from the inner side 26 to the outer side 25) on the circumferential surface 27 as well as a second (here planar) portion 33 on the second area 29 of the inner side 26, wherein the two portions 32, 33 (in FIG. 3) form an angle which is 90° here. However, the angle can also lie in the range of from 80 to 100°. Through the provision of these two portions 32 and 33, the advantage is achieved that undesired scattered light, which strikes the first portion 32, for example, and is not completely absorbed by it, is reflected to the second portion 33, as is represented schematically for a scattered light beam 34 in FIG. 3. Of course, a scattered light beam 35 which first strikes the second portion 33 and is not completely absorbed by it can also be further absorbed in a comparable manner since the reflection of this beam 35 strikes the first portion 32, which brings about a further absorption. Scattered light is thus suppressed very well with the result that the imaging properties of the whole endoscope lens system 5 are considerably improved. A greater contrast is achieved and undesired double or ghost images can be effectively prevented.

The shape of the light-absorbing coating 30 can be described as a hollow cylinder with a base comprising an opening, wherein the first portion 32 forms the wall of the hollow cylinder (e.g. with a circular outer contour or a circle as surface line) and the second portion 33 forms the base. Since the second portion 33 is annular (FIG. 4), it comprises the opening which is situated such that the concavely curved first area 28 is not coated with the light-absorbing coating 30. The surface line for the wall of the hollow cylinder does not have to be circular but can also have any other closed shape (e.g. elliptical, oval or even polygonal). The hollow cylinder can be an upright hollow cylinder or an inclined hollow cylinder. Furthermore, instead of a hollow cylinder, the shape of a hollow truncated cone, or another concave shape with a base which comprises the opening and a lateral surface, can also be implemented.

The first lens 7 can comprise an anti-reflection layer (not shown) on its outer side 25 and/or on the first area 28 of the inner side 26.

In the embodiment example described here, part of the second area 29 of the inner side 26 is in contact with the socket 24, as is shown in FIG. 2. In this case, the solderable layer 31 can also be applied to this part of the second area 29, wherein in turn the light-absorbing coating 30 is preserved underneath. A soldered connection with the socket 24 can thus also be realized in this area.

The endoscope 1 can be modified such that it does not comprise a socket 24. In this case, the first lens 7 is soldered directly to the optical tube 4, for example.

Figure 5:
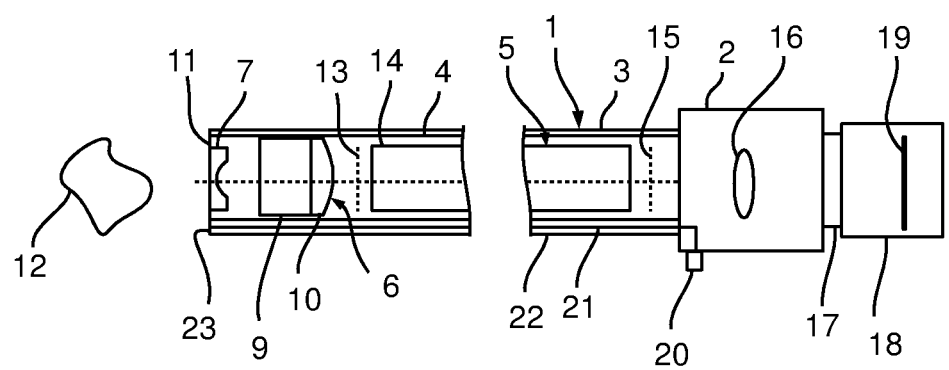
FIG. 5 is a sectional view of a further embodiment example of the endoscope in accordance with certain example embodiments.

The embodiment example described hitherto shows an endoscope 1 with a direction of view which is oblique vis-à-vis the direction of extension of the shaft 3. Of course, the endoscope 1 can also be formed as a forward view endoscope 1, as is shown schematically in FIG. 5. In this case, no deflection is necessary in the objective 6 with the result that here the objective 6 does not comprise a deflecting prism 8. Otherwise, the structure is identical to that of the already described endoscope 1 with an oblique direction of view.

Furthermore, the endoscope 1 can be formed such that an optical view (or an eyepiece) is provided instead of the camera 18 and the camera connection 17. Alternatively, the image sensor 19 can be arranged in the distal intermediate image plane 13. In this case, the inversion system 14 and the further lens system 16 can be omitted. The image data of the image sensor 19 can be transmitted, e.g. via a data connection extending through the shaft, to the main part 2, which comprises e.g. a digital display for the image data.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A lens for a distal end of an optical channel of an endoscope shaft, comprising:
    an outer side;
    an inner side; and
    a circumferential surface connecting the outer side and the inner side,
    wherein a light-absorbing coating is applied to the circumferential surface and an annular area of the inner side that is oriented parallel to the outer side,
    wherein a solderable layer is applied to the light-absorbing coating in the area of the circumferential surface such that the lens can be soldered in the distal end so that the distal end is sealed, and
    wherein the circumferential surface and the annular area of the inner side have a matte structure.

2. The lens according to claim 1, wherein the light-absorbing coating is a metallic coating.

3. The lens according to claim 1, wherein the inner side comprises a concavely curved portion.

4. The lens according to claim 1, wherein the solderable layer is also applied to the annular area of the inner side.

5. The lens according to claim 1, wherein the light-absorbing coating comprises chromium.

6. The lens according to claim 1, wherein the area of the light-absorbing coating formed on the circumferential surface forms, in a cross-sectional view through a diameter of the lens, an angle which lies in the range of from 80° to 100° with a portion of the light-absorbing coating formed on the annular area of the inner side.

7. The lens according to claim 1, wherein a portion of the light-absorbing coating formed on the annular area of the inner side is annular when seen in a direction normal to the inner side.

8. The lens according to claim 1, wherein the solderable layer comprises gold.

9. An endoscope, comprising:
   an endoscope shaft, comprising an optical channel including a distal end; and
   a lens according to claim 1,
   wherein the lens is soldered in the distal end via the solderable layer such that the distal end is sealed.

* * * * *